US00PP19668P2

(12) United States Plant Patent
Hambali

(10) Patent No.: US PP19,668 P2
(45) Date of Patent: Feb. 3, 2009

(54) ***AGLAONEMA* PLANT NAMED 'TWYAG0005'**

(50) Latin Name: *Aglaonema commutatum var. tricolor×A. rotundum*
Varietal Denomination: TWYAG0005

(75) Inventor: Gregori G. Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/903,059

(22) Filed: Sep. 20, 2007

(51) Int. Cl.
*A01H 5/00* (2006.01)

(52) U.S. Cl. ..... Plt./376
(58) Field of Classification Search ..... Plt./376
See application file for complete search history.

*Primary Examiner*—Anne Marie Grunberg
*Assistant Examiner*—Louanne C Krawczewicz Myers
(74) *Attorney, Agent, or Firm*—Jondle & Associates, P.C.

(57) ABSTRACT

A new *Aglaonema* plant particularly distinguished by having very dense, leafy, compact and upright branched plant habit, small to intermediate stature, very vigorous growth habit, profuse suckering and produces numerous axillary branches and dominantly green leaves on the upper leaf surface and reddish-green leaves on the lower surface, is disclosed.

1 Drawing Sheet

Genus and species: *Aglaonema commutatum* var. *tricolor×A. rotundum* hybrid.
Variety denomination: 'TWYAG0005'.

BACKGROUND OF THE NEW PLANT

The present invention comprises a new and distinct cultivar of *Aglaonema,* botanically known as *Aglaonema commutatum* var. *tricolor×A. rotundum* hybrid, and hereinafter referred to by the cultivar name 'TWYAG0005'. The new cultivar originated from a hybridization made in 1999 in Bogor, Indonesia. The female parent was an unknown individual plant of *A. commutatum* var. *tricolor* (patent status unknown), while the male parent was an unknown individual plant of *A. rotundum* (patent status unknown).

The new cultivar was created in Bogor, Indonesia and has been asexually reproduced repeatedly by vegetative cuttings and sucker division in Apopka, Fla. and Bogor, Indonesia over a 5-year period. The present invention has been found to retain its distinctive characteristics through successive asexual propagations.

Plant Breeder's Rights for this cultivar were applied for in the European Union in early September 2007. 'TWYAG0005' has not been made publicly available more than one year prior to filing of this application.

SUMMARY OF THE INVENTION

The following are the most outstanding and distinguishing characteristics of this new cultivar when grown under normal horticultural practices in Apopka, Fla. and Bogor, Indonesia.

1. Small to intermediate in stature;
2. Dense, leafy, compact and upright branched plant habit;
3. Leaves are dominantly green in color on the upper surface and reddish green on the lower surface;
4. Profuse suckering;
5. Very vigorous growth habit; and
6. Produces numerous axillary branches and leaves.

DESCRIPTION OF THE PHOTOGRAPHS

This new *Aglaone* a plant is illustrated by the accompanying photographs which show overall plant habit. The colors shown are as true as can be reasonably obtained by conventional photographic procedures.

DESCRIPTION OF THE NEW CULTIVAR

Figure 1:
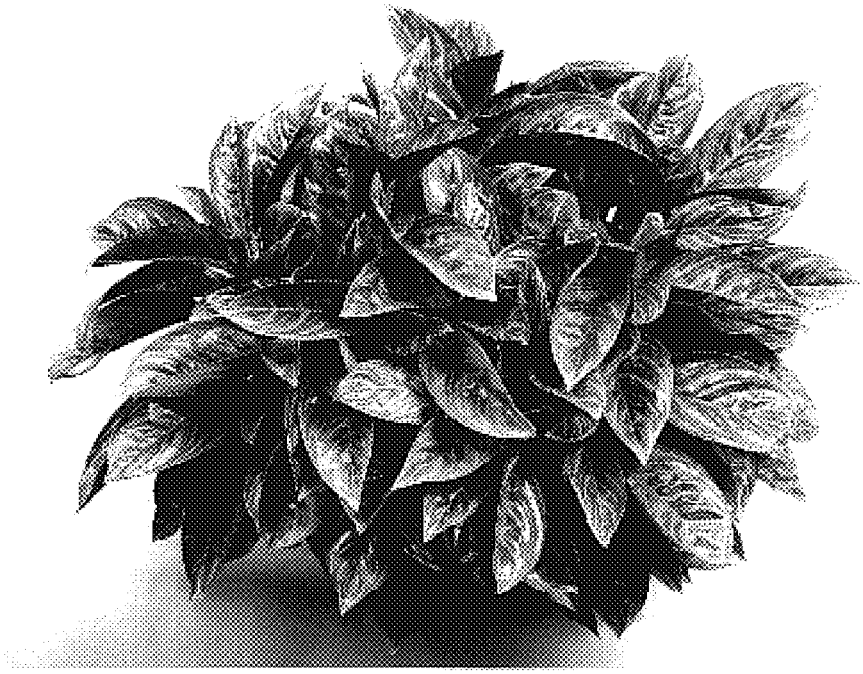
FIG. 1 shows the overall plant habit of the new plant.
Figure 2:
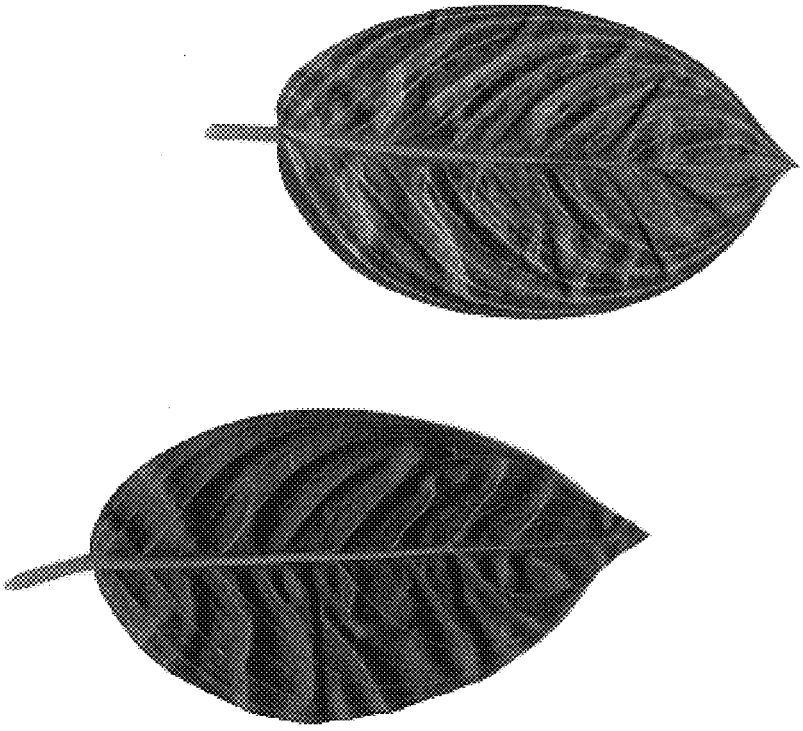
FIG. 2 shows the upper and lower surface of the mature leaves.

The following detailed description sets forth the distinctive characteristics of 'TWYAG0005'. The data which define these characteristics were collected from asexual reproductions carried out in Apopka, Fla. The plant history was taken on 16-month old plants started from a single 4-leaf rooted cutting, still in a vegetative state and grown in Apopka, Fla. Rooted cuttings were planted in 20-cm pots and grown in a greenhouse in May 2006. The average daily temperature was about 85° to 95° F. and the average nightly temperature was about 65° to 78° F. The plants were pinched twice. Color readings were taken under natural light. Color references are primarily to the R.H.S. Colour Chart of The Royal Horticultural Society of London (R.H.S.) (2001).

DETAILED BOTANICAL DESCRIPTION

Classification:
*Family.*—*Araceae*
*Botanical.*—*Aglaonema commutatum* var. *tricolor×A. rotundum* hybrid.
*Cultivar name.*—'TWAG0005'.
*Common name.*—Chinese Evergreen.

Parentage: The female parent is an unknown individual plant of *A. commutatum* var. *tricolor* and the male parent is an unknown individual plant of *A. rotundum.*

Growth:
*Form.*—Symmetrical, round, wider than tall; leaves lean outward.

*Growth and branching habit.*—Densely leafy, compact; upright branched growth habit (basal branching); small to intermediate in stature; very vigorous growth habit; plants produce numerous axillary branches and leaves.

*Height* (*from soil to top of leaf plane*).—28 cm to 32 cm.

*Diameter* (*area of spread, measured from leaf tip to leaf tip across the canopy*).—43 cm to 50 cm.

*Time to produce a finished plant.*—16-months starting from a single 4-leaf rooted cutting and pinched twice.

*Growth rate.*—More rapid than typical *Aglaonema* cultivars.

*Root description.*—Abundant, fleshy white roots with finer lateral branches.

*Number of divisions or clumps per year.*—About 6 to 10, 4-leaf cuttings per year.

*Durability of foliage to stresses.*—Leaves hold up well against damage from shipping and handling; plant is durable, excellent indoor keeping quality.

*High temperature tolerance.*—To about 104° F. for several hours without damage.

*Low temperature tolerance.*—To about 55° F. for several hours without damage.

Stems:

*Number of branches per plant.*—25.

*Length* (*from soil line to the junction of the newest two leaves*).—17 cm.

*Diameter* (*measured from the midpoint*).—1.1 cm.

*Internode length.*—1.0 cm to 1.6 cm.

*Color.*—Immature: RHS 144C to RHS N144D. Mature: RHS 146D with area of RHS 146A. Oldest stems: RHS 147A.

*Appearance* (*shape*).—Columnar, cylindrical upright.

*Aspect.*—Vertical, upright.

*Strength.*—Sturdy, strong, somewhat flexible.

*Axillary buds.*—Shape and arrangement: Elliptic, flat, alternate. Length: 0.4 cm. Width: 0.25 cm. Color: RHS 155A (white), tinged with RHS 65D (pale-pink).

Leaves:

*Arrangement and type.*—Alternate, single leaf per petiole, simple, arranged in a spiral along the stem.

*Quantity of leaves per stem.*—10.

*Immature leaf* (*new expanded leaf*).— *Color: Upper surface: Base color much darker and greener than but closest to RHS* 147A; Herringbone pattern of between RHS 191A and RHS 189A (dark silver-green). Lower surface: Entirely between RHS N186A and RHS 187A, tinged with RHS 147A (green).

*Mature leaf.*—Color: Upper surface: Base color much darker and greener than but closest to RHS N189A; Herringbone pattern with RHS 189A (dark silver-green). Lower surface: Entirely between RHS N186A and RHS 187A, tinged with RHS 147A (green).

*Length.*—12.5 cm to 16.5 cm.

*Width.*—General: The leaf blade folds upward along the midrib. Flattened: 7.3 cm to 7.9 cm. Not flattened: 4.0 cm to 6.5 cm.

*Shape.*—Elliptic to ovate.

*Apex.*—Acute to acuminate.

*Base.*—Obtuse.

*Margin.*—Smooth, entire, mostly flat with some broad undulations.

*Texture.*—Upper surface: Smooth; new leaves are shiny; mature leaves are shiny to glossy; Lower Surface: Smooth; New leaves are glossy; mature leaves are glossy to dull; the leaf blade is convex between the main veins giving the leaf a textured and somewhat puckered appearance.

*Pubescence.*—None.

*Venation pattern.*—Pinnate, radiating outward from the midrib in a herringbone arrangement.

*Venation color* (*immature leaf*).—Upper surface: Primary veins: Between RHS 182D and RHS 63C. Midrib: RHS 65D tinged with RHS 53D especially near the apex. Lower surface: Primary veins: RHS 53C. Midrib-proximal: Between RHS 147A and RHS 148A. Midrib-distal: RHS 51B.

*Venation color* (*Mature leaf*).—Upper surface: Primary veins: RHS 191A tinged with RHS 53D. Midrib: RHS 182D flushed with RHS 185A to RHS 185B especially near the apex. Lower surface: Primary veins: RHS 185B to 185C. Midrib-proximal: Much darker than RHS 147A. Midrib-distal: RHS 184C.

*Petioles.*—Aspect: Vertical upright when newly expanded, becoming curved outward and about 45° with maturity. Length: 7.0 cm. Diameter: Distal: 0.3 cm. Proximal (petiole and petiole sheath clasps the stem proximally): Flattened: 2.5 cm. Natural diameter: 1.1 cm. Color: Distal: Much darker than, but closest to RHS 147A. Proximal: Between RHS 147A and RHS 146B. Area adjacent to stem: RHS 150D tinged with RHS 146D. Wing length: 5.8 cm. Wing diameter: Mid-point: 0.6 cm. Base: 1.1 cm. Depth: 0.50 cm. Wing color: Inside: Between RHS 147B and 155C. Outside: Distal: RHS 147A tinged with RHS 183B. Proximal: RHS 150D tinged with RHS 146C to RHS 146D. Area adjacent to stem: RHS 155C.

Inflorescence: None observed.

Fruit and seed set: None observed.

Disease and insect resistance: Typical of *Aglaonema;* no particular susceptibility or resistance to pests or diseases noted.

COMPARISON WITH PARENTAL AND COMMERCIAL CULTIVARS

'TWYAG0005' differs from the female parent, an unknown individual plant of *A. commutatum* var. *tricolor* plant in that 'TWYAG0005' has green petioles, while the female parent has light pink petioles. In addition, 'TWYAG0005' has an elliptical leaf shape, while the female parent has an elliptical to oblong leaf shape.

'TWYAG0005' differs from the male parent, an unknown *A. rotundum* plant in that 'TWYAG0005' has an elliptical leaf shape, while the male parent has an ovate leaf shape. In addition, 'TWYAG0005' has profuse suckering, while the male parent has moderate to sparse suckering.

'TWYAG0005' differs from the commercial variety 'Red Gold' (unpatented) in that 'TWYAG0005' has a reddish-green color on the lower surface of the leaves, while 'Red Gold' has a pale yellowish-green color on the lower surface of the leaves. 'TWYAG0005' has profuse suckering, while 'Red Gold' has moderate to sparse suckering. In addition, the leaf shape of 'TWYAG0005' is elliptical, while the leaf shape of 'Red Gold' is broadly elliptical to ovate-elliptical.

I claim:

1. A new and distinct cultivar of *Aglaonema* plant as shown and described herein.

* * * * *